US012766121B2

(12) United States Patent
Wang et al.

(10) Patent No.: US 12,766,121 B2
(45) Date of Patent: Oct. 20, 2026

(54) METHOD FOR TREATING AND/OR PREVENTING EPILEPSY AND REDUCING SIDE EFFECT OF ANTI-EPILEPTIC DRUG BY USING CYNARIN

(71) Applicant: FU JEN CATHOLIC UNIVERSITY, New Taipei City (TW)

(72) Inventors: Su-Jane Wang, New Taipei City (TW); Chi-Feng Hung, New Taipei City (TW); Wun-Jing Pan, New Taipei City (TW)

(73) Assignee: FU JEN CATHOLIC UNIVERSITY, New Taipei City (TW)

( * ) Notice: Subject to any disclaimer, the term of this patent is extended or adjusted under 35 U.S.C. 154(b) by 364 days.

(21) Appl. No.: 18/658,061

(22) Filed: May 8, 2024

(65) Prior Publication Data

US 2025/0302791 A1 Oct. 2, 2025

(30) Foreign Application Priority Data

Apr. 1, 2024 (TW) .................................. 113112411

(51) Int. Cl.
*A61K 31/216* (2006.01)
*A61K 31/55* (2006.01)
*A61P 25/08* (2006.01)

(52) U.S. Cl.
CPC ............ *A61K 31/216* (2013.01); *A61P 25/08* (2018.01); *A61K 31/55* (2013.01)

(58) Field of Classification Search
None
See application file for complete search history.

(56) References Cited

PUBLICATIONS

Sarlo et al. "Brain concentrations of glutamate and GABA in human epilepsy: A review" Seizure: European Journal of Epilepsy 91 (2021) 213-227 (Year: 2021).*
Kim et al. "Natural Products as Potential Anticonvulsants: Caffeoylquinic Acids" Arch Pharm Res vol. 35, No. 3, 389-392, 2012 (Year: 2012).*
Cheng-Wei Lu et al., "Cynarin, a caffeoylquinic acid derivative in artichoke, inhibits exocytotic glutamate release from rat cortical nerve terminals (synaptosomes)", Neurochemistry International, 167, May 8, 2023, 8 pages.

* cited by examiner

*Primary Examiner* — Adam C Milligan
*Assistant Examiner* — Jed A Kucharczk
(74) *Attorney, Agent, or Firm* — Muncy, Geissler, Olds & Lowe, P.C.

(57) ABSTRACT

The present disclosure provides a method for treating and/or preventing epilepsy and reducing side effects of the anti-epileptic drug by using Cynarin. The Cynarin of the present disclosure achieves the effect of treating and/or preventing epilepsy and reducing side effects of the anti-epileptic drug through various efficacy experiments.

12 Claims, 4 Drawing Sheets

Racine scale

| Seizure stage | Behavioral expression |
|---|---|
| 0 | No symptoms |
| 1 | Facial clonus |
| 2 | Nodding and wet dog shaking |
| 3 | Forelimb clonus |
| 4 | Forelimb clonus with rearing |
| 5 | Rearing, jumping and falling |

METHOD FOR TREATING AND/OR PREVENTING EPILEPSY AND REDUCING SIDE EFFECT OF ANTI-EPILEPTIC DRUG BY USING CYNARIN

CROSS-REFERENCE TO RELATED APPLICATION

This application claims priority of Taiwan patent application No. 113112411, filed on Apr. 1, 2024, the content of which is incorporated herein in its entirety by reference.

BACKGROUND OF THE INVENTION

1. Field of the Invention

The present invention relates to a method for treating and/or preventing epilepsy and reducing side effects of the anti-epileptic drug by using Cynarin (CYN).

2. The Prior Art

Epilepsy is a common neurological disease. It is the fourth largest neurological disease after stroke, migraine and Alzheimer's disease, affecting as many as 70 million people worldwide. This disease is characterized by abnormal discharge of brain nerve cells leading to repetitive, spontaneous and unpredictable attacks, mainly occurring in the cerebral cortex and hippocampus areas. The causes of epilepsy may be related to congenital or acquired brain lesions, such as intracerebral trauma, infection, stroke, and tumors. However, about 70% of epilepsy patients cannot find any cause. Although the cause of most epilepsy is unknown, it is generally believed that it may be due to an imbalance between the inhibitory nervous system (i.e., γ-aminobutyric acid (GABA) system) and the excitatory nervous system (i.e., the glutamate system) in the brain, resulting in over-excitability of nerve cells.

The mechanism of anti-epileptic drugs currently used to control epileptic seizures is mainly to regulate the stability of nerve cells by blocking sodium ion channels and directly inhibiting the excitability of nerve cells (e.g., phenytoin and Carbamazepine); and inhibiting glutamate (e.g., lamotrigine and felbamate) or enhancing GABA (e.g., benzodiazepines, tiagabine, and vigabatrin). However, although there are nearly thirty drugs currently used to treat epilepsy, approximately one-third of epilepsy patients are resistant to anti-epileptic drugs and require high doses. In addition, the side effects of drugs, such as allergies, increased burden on the liver, dizziness and headaches, also limit patients' compliance with anti-epileptic drugs. Therefore, it is necessary to find and develop more effective and safer new drugs for the treatment of epilepsy. Currently, natural products have become the target of anti-epileptic drug research.

In order to solve the above-mentioned problems, those skilled in the art urgently need to develop a novel and more effective pharmaceutical composition for treating and/or preventing epilepsy and reducing side effects of the anti-epileptic drug for the benefit of a large group of people in need thereof.

SUMMARY OF THE INVENTION

A primary objective of the present invention is to provide a method for treating and/or preventing epilepsy, comprising administering to a subject in need thereof a pharmaceutical composition comprising an effective amount of Cynarin (CYN).

According to an embodiment of the present invention, the CYN prolongs the duration of epileptic seizure.

According to an embodiment of the present invention, the CYN reduces the severity of epileptic seizure.

According to an embodiment of the present invention, the CYN reduces the number loss of nerve cells.

According to an embodiment of the present invention, the effective amount of CYN is 5-100 mg/kg.

Another objective of the present invention is to provide a method for reducing side effects of an anti-epileptic drug, comprising administering to a subject in need thereof a pharmaceutical composition comprising an effective amount of Cynarin (CYN).

According to an embodiment of the present invention, the anti-epileptic drug is Carbamazepine (CBZ).

According to an embodiment of the present invention, the effective amount of CYN is 5-25 mg/kg.

According to an embodiment of the present invention, the pharmaceutical composition is in a dosage form for oral administration.

According to an embodiment of the present invention, the pharmaceutical composition is in a dosage form for parenteral administration.

In summary, the CYN of the present invention achieves the effect on treating and/or preventing epilepsy and reducing side effects and drug resistance of the anti-epileptic drug as illustrated in the following examples.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
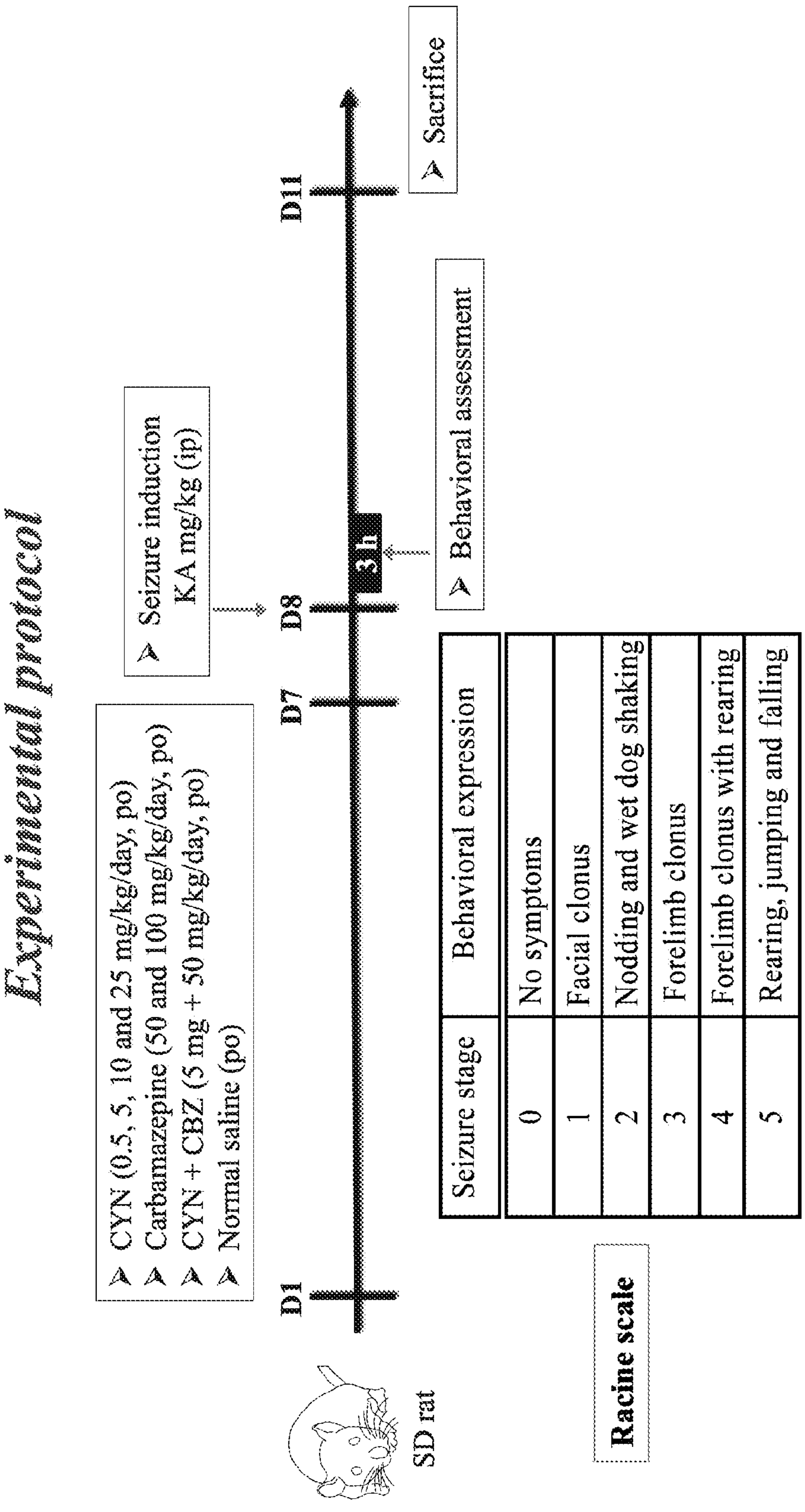
FIG. 1 is the experimental protocol of the animal experiment of Cynarin (CYN), wherein p.o. (po) means oral administration, and i.p. (ip) means intraperitoneal injection.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

As used herein, the term "treating" or "treatment" refers to alleviating, reducing, ameliorating, relieving, or controlling one or more clinical signs of a disease or disorder, and lowering, stopping, or reversing the progression of severity regarding the condition or symptom being treated.

The term "preventing" refers herein to inhibiting progression of a disease, disorder or condition from developing in a subject. In some embodiments, the term "preventing" refers herein to attenuating the onset and development of disease symptoms. In some cases the subject may be at risk for developing the disease, but has not yet been diagnosed as having the disease.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

The pharmaceutical composition according to the present invention can comprise a pharmaceutically acceptable carrier which is widely used in pharmaceutical manufacturing technology. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar solution, aqueous solution containing alcohol, and combinations thereof.

According to the present invention, Cynarin (CYN) is a caffeoylquinic acid derivative, mainly derived from artichoke (*Cynara scolymus* L.), Asteraceae, and has a variety of pharmacological properties, including antioxidant, anti-inflammatory, anti-cancer, hepatoprotective, immunomodulatory and cholesterol-lowering activity. However, there is currently a lack of research exploring the activity of Cynarin on the central nervous system, and its role in epilepsy has not yet been studied.

The reason why the present invention selects kainic acid (KA) as an epilepsy model is that the increased concentration of excitatory neurotransmitters (such as glutamate) in the central nervous system is considered to be related to the pathological mechanism of epilepsy. Excess glutamate in the central nervous system can lead to calcium imbalance, triggering oxidative stress, neuroinflammation, mitochondrial dysfunction, and ultimately neuronal death, which may further cause epileptic seizures. Kainic acid (KA) can simulate the hyperexcitable state in the brain during epilepsy. KA is an analog of glutamate. By activating the receptors of glutamate and KA, it triggers abnormal neuron discharge and produces characteristics similar to human epileptic seizures, making it an ideal choice for studying epilepsy mechanisms and evaluating therapeutic effects. Therefore, this example uses the KA-induced epilepsy model in rats to find that Cynarin has anti-epileptic effects.

Experimental animals are as follows. Male Sprague-Dawley rats (weight 200-250 g) purchased from BioLASCO in Taipei were housed in the Animal Center of Fu Jen Catholic University and maintained in a 12-h light/dark cycle with food and water available ad libitum. Rats were allowed to acclimate to laboratory conditions for at least 3 days before the start of the experiment.

The sources of drugs are as follows. The dosage range of Cynarin (CYN) used in the study is from 0.5 to 25 mg/kg and was purchased from TAUTO BIOTECH, China, with a purity of 98.0%. Kainic acid (KA) used in the experiment was purchased from Sigma-Aldrich (Missouri, USA) at 15 mg/kg. In addition, the anti-epileptic drug Carbamazepine (CBZ), in doses ranging from 50 to 100 mg, was also obtained from Sigma-Aldrich.

Current anti-epileptic drugs still have some limitations. For example, approximately 30% of patients do not respond to existing treatments. The research focuses on the following directions: A. Oral effective dose of Cynarin against epilepsy; B. Optimal combination of Cynarin and CBZ; C. Reducing side effects. For example, when Cynarin is used alone, anti-epileptic effects comparable to anti-epileptic drugs (such as CBZ) can be obtained. In other words, Cynarin can be used to replace anti-epileptic drugs. In addition, when Cynarin is used in combination with anti-epileptic drugs, the dose of anti-epileptic drugs (such as CBZ) can be further reduced while achieving the anti-epileptic effect. Therefore, whether Cynarin is used alone or in combination with anti-epileptic drugs, the side effects of anti-epileptic drugs can be reduced.

Therefore, the present invention initially utilizes kainic acid (KA) to induce epilepsy model in rats and finds that Cynarin affects improving epileptic behavior and brain nerve cell damage in animals. This result proves that Cynarin has anti-epileptic effects.

Example 1

Effect of Cynarin (CYN) on Preventing and Treating Epilepsy

The experimental design of the present invention is as follows. Cynarin pretreatment reduces epileptic behavior in animals induced by kainic acid (KA). Cynarin was administered orally once a day in different dosage groups (CYN 0.5, 5, 10, and 25 mg/kg) for seven days, followed by intraperitoneal injection of kainic acid (KA 15 mg/kg) to induce epilepsy, and the epileptic seizure behavior of rat was observed for three hours. Behavioral scoring was based on the Racine scale (1972), see FIG. 1.

Experimental grouping is as follows. Normal saline control group, KA 15 mg/kg group (n=8), CBZ 50 mg/kg group (n=5), CBZ 100 mg/kg group (n=17), Cynarin 0.5 mg/kg group (n=5), Cynarin 5 mg/kg group (n=7), Cynarin 10 mg/kg group (n=8), Cynarin 25 mg/kg group (n=5), and combination of the anti-epileptic drug (CBZ): CYN 5 mg/kg+CBZ 50 mg/kg group (n=11).

The experimental protocol for Racine scale behavioral scoring is as follows. The rats' epileptic seizure activity was continuously monitored for 3 hours, and epileptic behavior was scored according to the 1972 Racine scale. 0 point: No symptoms; 1 point: Facial clonus; 2 points: Nodding and wet dog shaking; 3 points: Forelimb clonus; 4 points: Forelimb clonus with rearing; 5 points: rearing, jumping and falling.

Statistical analysis is as follows. The statistical analysis and graphics production used in the experiment were performed using GraphPad Prism v10.0.3 software (GraphPad Software located in La Jolla, California, USA). Data are expressed as mean±standard error (SEM). Statistical significance was determined by one-way analysis of variation (ANOVA), combined with Bonferroni's post hoc test, and a p-value less than 0.05 was used as the criterion for significant differences.

Figure 2A:
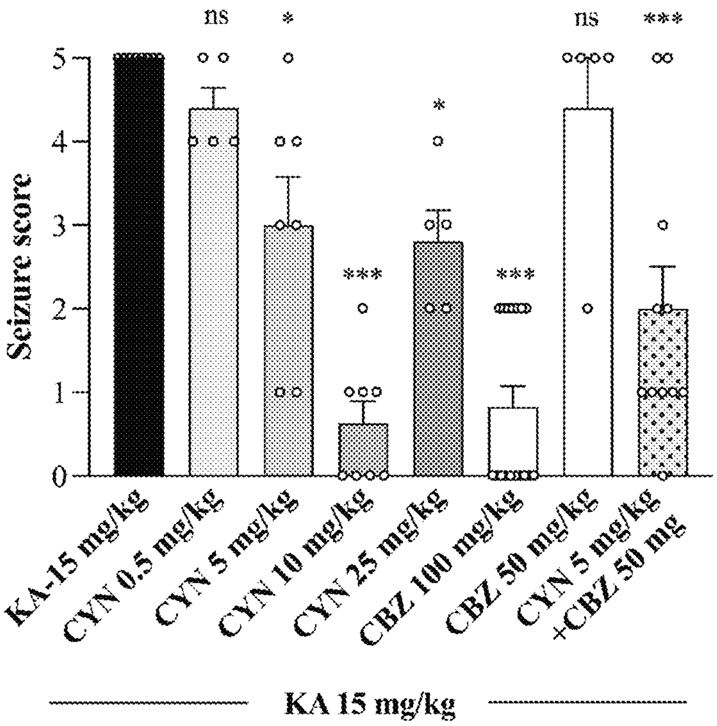
FIGS. 2A and 2B show CYN reduces KA-induced seizure behavior in rats. The rats were pretreated either with normal saline (control), or CYN (0.5-25 mg/kg/day, p.o.), or CBZ (50 or 100 mg/kg/day, p.o.) or CYN 5 mg/kg/day+CBZ 50 mg/kg/day (p.o.) for 7 days before KA injection (15 mg/kg, i.p.). Seizure score (2A) and seizure latency (2B) were assessed during 1-4 h after KA administration, according to the experimental method. Data are expressed as mean±SEM. ***P<0.001, *P<0.05, ns-no significant compared to KA group. Each data point represents the result of a single animal.
Figure 2B:
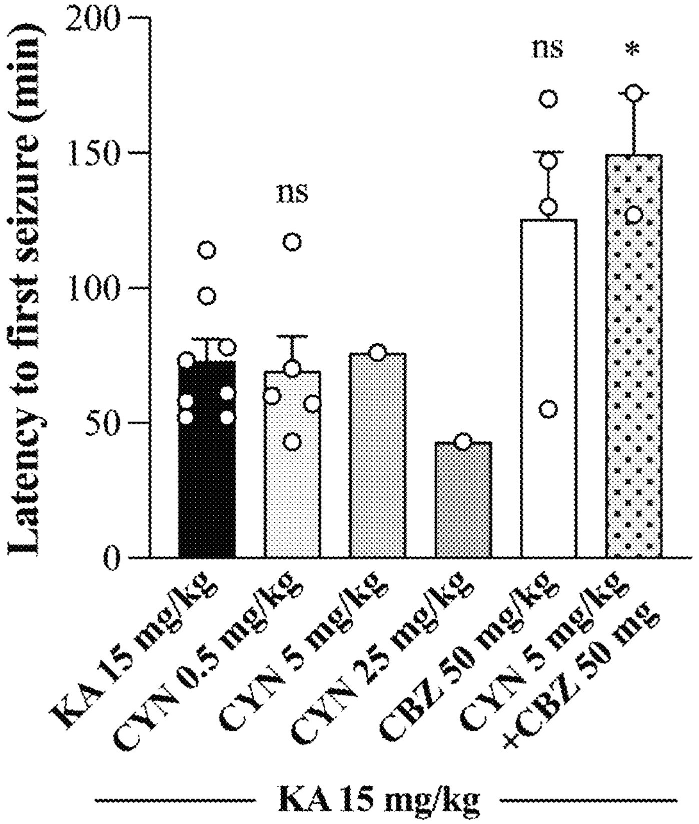

FIGS. 2A and 2B show that CYN reduces KA-induced seizure behavior in rats. The rats were pretreated either with normal saline (control), or CYN (0.5-25 mg/kg/day, p.o.), or CBZ (50 or 100 mg/kg/day, p.o.) or CYN 5 mg/kg/day+CBZ 50 mg/kg/day (p.o.) for 7 days before KA injection (15 mg/kg, i.p.). According to the experimental method, the severity of epilepsy (FIG. 2A) and the latency to onset of epilepsy (FIG. 2B) were assessed within 3 hours after KA administration. Data are expressed as mean±SEM. Different degrees of asterisks represent statistically significant differences, where ***P<0.001 indicates extremely significant differences compared to the KA group, *P<0.05 represents a significant difference, and 'ns' represents no significant difference. Each point represents a single animal.

1-1. Cynarin Replaces Anti-Epileptic Drugs

The result indicate that in the pre-oral administration of CYN at doses of 0.5, 5, 10, and 25 mg/kg, as shown in FIGS. 2A and 2B, CYN at 0.5 mg/kg did not affect the epilepsy induced by KA. Among the doses of CYN 5, 10, and 25 mg/kg, CYN at 10 mg/kg has the strongest inhibitory effect on epileptic seizure behavior in animals, which is equivalent to the effect of the anti-epileptic drug CBZ (100 mg/kg). Therefore, CYN has potential as an anti-epileptic drug.

1-2. Cynarin Co-Administered with Anti-Epileptic Drugs

In order to prove that Cynarin can assist in the treatment of epilepsy and reduce the side effects of anti-epileptic drugs, this embodiment uses the KA epilepsy animal model to evaluate the oral effective dose of Cynarin against epilepsy, and optimal combination of Cynarin and Carbamazepine (CBZ).

FIGS. 2A and 2B show that when Cynarin (CYN) is used at a low dose (5 mg/kg) in combination with Carbamazepine (CBZ) 50 mg/kg, its inhibitory effect on epileptic behavior is comparable to that of CBZ 100 mg/kg or CYN 10 mg/kg alone. This shows that only a lower dose of CYN (5 mg/kg) can be used to reduce the dose of the anti-epileptic drug CBZ by 50%, thus reducing the side effects of anti-epileptic drugs.

Example 2

Effect of Cynarin (CYN) Pretreatment on Cell Death of Hippocampal Neurons in Kainic Acid (KA)-Treated Rats In this example, rats were divided into four groups: a control group, a KA-only (15 mg/kg) treatment group, a Cynarin (CYN) (10 mg/kg) plus KA (15 mg/kg) treatment group, and a triple treatment group consisting of Cynarin (CYN) (5 mg/kg), Carbamazepine (CBZ) (50 mg/kg), and KA (15 mg/kg). During the experiment, except for the control group, rats in each group were administered Cynarin orally once daily for seven days. Then, on the eighth day, all experimental groups, except the control group, were further treated by intraperitoneal injection of KA (15 mg/kg).

Figure 3A:
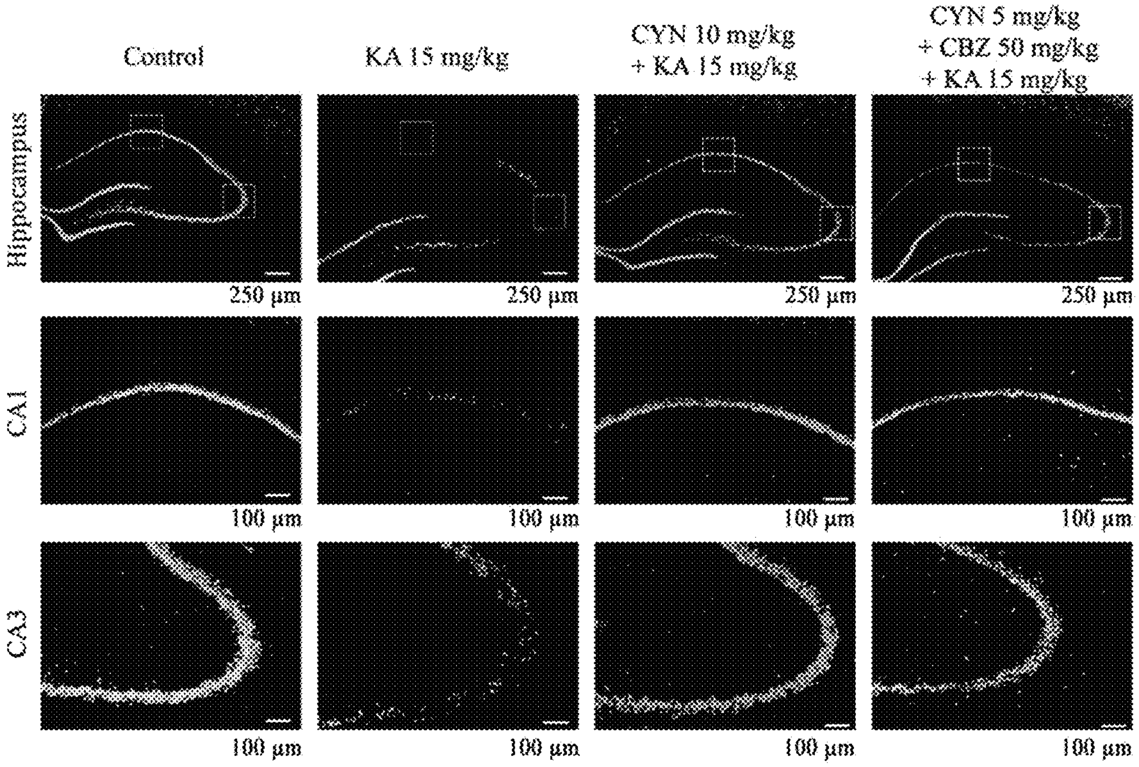
FIGS. 3A and 3B show the effect of Cynarin (CYN) pretreatment on kainic acid (KA)-induced nerve cell death in the hippocampus of rats. (3A) Representative images of Neuronal nuclei (NeuN) staining at 72 h after KA i.p. injection. (3B) Semiquantitative analysis of NeuN-positive cells in the CA1 and CA3 regions. Data are mean±SEM (n=5 per group). ***, p<0.001 vs. control group. #, p<0.001 vs. KA group.
Figure 3B:
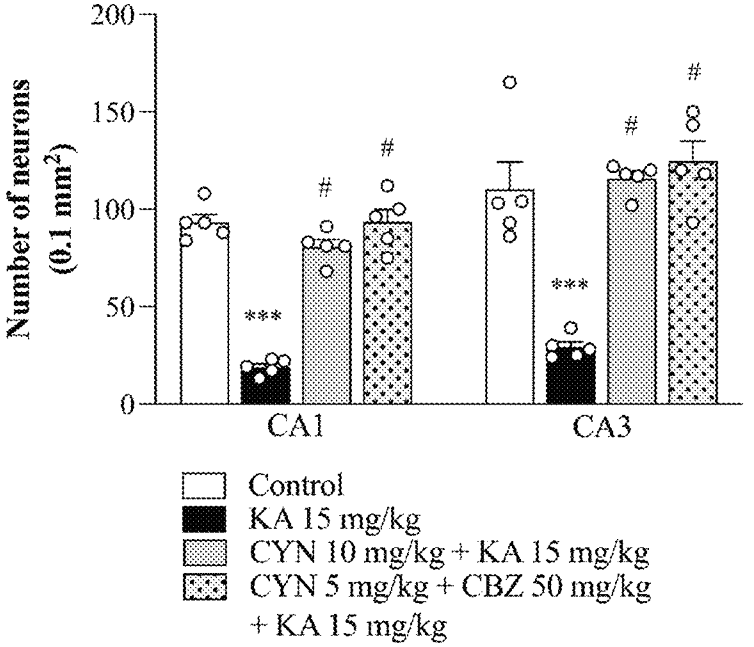

FIGS. 3A and 3B show the effect of Cynarin (CYN) pretreatment on kainic acid (KA)-induced nerve cell death in the hippocampus of rats. (3A) Representative images of Neuronal nuclei (NeuN) staining at 72 h after KA i.p. injection. (3B) Semiquantitative analysis of NeuN-positive cells in the CA1 and CA3 regions. Data are mean±SEM (n=5 per group). ***, p<0.001 vs. control group. #, p<0.001 vs. KA group.

Neuronal nuclei (NeuN) staining also found that the number of hippocampal CA1/CA3 nerve cells in the KA group was significantly reduced. This phenomenon can also be reduced by pretreatment with Cynarin (10 mg/kg) or Cynarin (5 mg/kg) combined with Carbamazepine (CBZ) (50 mg/kg) (see FIGS. 3A and 3B). These results show that Cynarin pretreatment can prevent neuronal cell damage caused by KA. The above animal experiment results confirm that Cynarin may prevent neurological damage caused by KA-induced epilepsy.

According to the results of the embodiment, Cynarin has the effect of inhibiting epileptic behavior whether used alone (10 mg/kg) or combined with clinical medication (CYN 5 mg/kg+CBZ 50 mg/kg). The present invention can solve the dilemma that long-term use of anti-epileptic drugs would produce many side effects or provide new treatment options for patients who have no therapeutic response to existing anti-epileptic drugs.

In summary, the CYN of the present invention achieves the effect of treating and/or preventing epilepsy and reducing side effects and drug resistance of the anti-epileptic drug as illustrated in the above examples.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating and/or preventing epilepsy, comprising administering to a subject in need thereof a pharmaceutical composition comprising an effective amount of cynarin (CYN).

2. The method according to claim 1, wherein the CYN prolongs the duration of epileptic seizure.

3. The method according to claim 1, wherein the CYN reduces the severity of epileptic seizure.

4. The method according to claim 1, wherein the CYN reduces the number of loss of nerve cells.

5. The method according to claim 1, wherein the effective amount of CYN is 5-100 mg/kg.

6. The method according to claim 1, wherein the pharmaceutical composition is in a dosage form for oral administration.

7. The method according to claim 1, wherein the pharmaceutical composition is in a dosage form for parenteral administration.

8. A method for reducing side effects of an anti-epileptic drug, comprising administering to a subject in need thereof a pharmaceutical composition comprising an effective amount of cynarin (CYN).

9. The method according to claim 8, wherein the anti-epileptic drug is carbamazepine (CBZ).

10. The method according to claim 8, wherein the effective amount of CYN is 5-25 mg/kg.

11. The method according to claim 8, wherein the pharmaceutical composition is in a dosage form for oral administration.

12. The method according to claim 8, wherein the pharmaceutical composition is in a dosage form for parenteral administration.

* * * * *